US00PP29875P3

(12) United States Plant Patent
Olesen

(10) Patent No.: US PP29,875 P3
(45) Date of Patent: Nov. 27, 2018

(54) MINIATURE ROSE PLANT NAMED 'POULPAR084'

(50) Latin Name: ***Rosa* hybrid**
Varietal Denomination: Poulpar084

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 52 days.

(21) Appl. No.: 14/756,265

(22) Filed: Aug. 20, 2015

(65) Prior Publication Data

US 2017/0055386 P1 Feb. 23, 2017

(51) Int. Cl.
*A01H 5/02* (2018.01)

(52) U.S. Cl.
USPC ..... Plt./118

(58) Field of Classification Search
USPC ..... Plt./118
See application file for complete search history.

(56) References Cited

PUBLICATIONS

Indoor Roses by Poulsen Main Varieties 2013.*
PLUTO Plant Variety Database Aug. 10, 2016.*

* cited by examiner

*Primary Examiner* — Annette H Para

(57) ABSTRACT

A new garden rose plant of the Miniature class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar084'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpar084', originated as a single seedling from the stated cross.

The new variety may be distinguished from its male pollen parent and female seed parent primarily by the following characteristics. The female seed parent is more compact than the new plant. The male pollen parent is about 40 cm in height while the new plant is about 25 cm in height.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar084' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar084' was selected in the spring of 2008 by the inventor as a single plant from the progeny of the aforementioned hybridization.

Asexual reproduction of 'Poulpar084' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpar084' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar084'. Specifically illustrated in the drawing are flowers at various stages of development, flower in parts, leaves, and stems. Plants shown are 1 year old.

DETAILED DESCRIPTION OF THE VARIETY

The following is a description of 'Poulpar084', as observed in its growth in in a field nursery in Marion County, Oreg. Observed plants are 1 years of age, and were grown on their own roots. Color references are made using The Royal Horticultural Society (London, England) Colour Chart, 2001, except where common terms of color are used.

For a comparison, several physical characteristics of the rose variety 'Poulpar065', U.S. Plant Pat. No. 23,822 are compared to 'Poulpar084' in Chart 1.

CHART 1

| | 'Poulpar084' | 'Poulpar065' |
|---|---|---|
| Petal Count | 60 | 80 to 90 |
| Flower Diameter | 45 mm | 50 to 55 mm |
| General Tonality of Flower Color | Yellow Group 13B | Yellow Group 10B with intonations of Yellow Group 13C |

FLOWER AND FLOWER BUD

Blooming habit: Continuous.

Flower bud:

*Size.*—Upon opening, 20 mm in length from base of receptacle to end of bud. Bud diameter is 17 mm.

*Bud form.*—Urceolate.

*Bud color.*—As sepals divide petals are Yellow Group 5B.

*Sepal inner surface.*—Color: Yellow-Green Group 144A. Surface: Smooth, moderately pubescent.

*Sepal outer surface.*—Color: Yellow-Green Group 144A with intonations of Greyed-Orange Group 166A. Texture: Somewhat rough.

*Sepal shape.*—Apex: Cirrhose. Base: Flat at union with receptacle.

*Sepal margin.*—Margins have moderate to strong foliaceous appendages on three of the five sepals.

*Sepal size.*—22 mm long by 12 mm wide.

*Receptacle.*—Texture: Smooth. Size: 5 mm in height by 7 mm wide. Color: Yellow-Green Group 144B with intonations of Greyed-Purple Group 183B. Shape: Funnel.

*Pedicel.*—Surface: Somewhat pubescent and Smooth. Length: 17 mm. Diameter: 2 to 3 mm. Color: Yellow-Green Group 144B with intonations of Greyed-Purple Group 184A. Strength: Strong.

*Peduncle.*—Length: 10 to 30 mm. Diameter: 2 to 3 mm. Color: Yellow-Green Group 146B with intonations of Greyed-Orange Group 166A.

Flower bud development: Flower buds are borne in clusters of 3 up to 5 flower buds per stem, resembling a corymb.

Flower bloom:

*Fragrance.*—Moderate floral scent.

*Duration.*—The blooms have a duration on the plant of approximately 21 days. Petals do not fall cleanly away from plant after flowers have fully matured.

*Size.*—Flower diameter is 60 mm when open. Flower depth is 27 mm.

*Flower shape.*—General shape is a rosette with many overlapping peals.

*Shape of flower, side view.*—The upper portion is flattened convex. The lower portion is flat.

Petalage: Under normal conditions, flowers have 45 petals total, 3 to 5 of which are petaloids.

General tonality of flower: Open flowers are Yellow Group 13B.

Petal color:

*Upon opening, outer petals.*—Upper surface: Yellow Group 12A. Lower surface: Yellow-Orange Group 14C mixed with Yellow Group 10B. Margins have intonations of Orange-Red Group N34C.

*Upon opening, inner petals.*—Upper surface: Yellow Group 12A. Lower surface: Yellow-Orange Group 14C mixed with Yellow Group 10B.

*After opening, outer and inner petals.*—Upper surface: Yellow Group 10B with intonations of Yellow Group 11A at base. Lower surface: Yellow Group 10B with intonations of Yellow Group 11A.

Petals:

*Petal reflex.*—Weak.

*Margin.*—Entire with a point at the center. Moderate undulations of margin observed.

*Shape.*—Generally broad elliptic. Apex shape: Cuspidate. Base shape: Acute.

*Size.*—31 mm (l) 28 mm (w).

*Texture.*—Smooth.

*Thickness.*—Average.

Petaloids:

*Size.*—10 mm (l) by 5 mm (w).

*Quantity.*—3 to 5.

*Shape.*—Irregular with crumpled margins. Base and apex are acute.

*Color.*—Yellow Group 13C on upper and lower surface.

Reproductive organs:

*Pollen.*—None observed.

*Anthers.*—Size: 2 mm in length. Color: Greyed-Yellow Group 162D. Quantity: on average.

*Filaments.*—Color: Yellow Group 12A. Length: 4 mm.

*Pistils.*—Length: 5 mm. Quantity: 25 on average.

*Stigmas.*—Color: Greyed-Yellow Group 162D.

*Styles.*—Color: Green-White Group 157A.

*Location of stigmas.*—Superior in location relative to the length of the filaments and the height of the anthers.

*Hips.*—None Observed.

PLANT

Plant growth: Upright. Plants are 25 cm in height, and 25 cm wide.

Stems:

*Color.*—Juvenile growth: Yellow-Green Group 146C with intonations of Greyed-Purple Group 184A. Mature growth: Yellow-Green Group 144A.

*Length.*—On average, canes are 15 cm from the base of the plant to the flowering portion.

*Diameter.*—8 mm.

*Internodes.*—On mature canes, there is an average distance of 28 mm between nodes.

*Surface texture.*—Young wood: Smooth. Older wood: Smooth.

Long prickles:

*Incidence.*—6 prickles per 10 cm of stem.

*Size.*—Average length of prickles on mature stems is 9 mm.

*Shape.*—Upper portion is linear. Lower portion is concave.

*Color.*—Juvenile prickles: Greyed-Purple Group 185B. Mature prickles: Greyed-Red Group 178B.

Plant foliage:

*Compound leaf.*—110 mm (l)×90 mm (w).

*Quantity.*—3 to 4 leaves per 10 cm of stem on average.

*Color of juvenile foliage.*—Upper side: Yellow-Green Group 146C with anthocyanin at margins Greyed-Red Group 178A. Lower side: Yellow-Green Group 146C with anthocyanin at margins Greyed-Red Group 178A.

*Color of mature foliage*.—Upper side: Yellow-Green Group 147A. Lower side: Yellow-Green Group 146B.

Plant leaves and leaflets:

*Stipules*.—Size: 17 mm in length. Quantity: 2 per compound leaf. Shape: Linear, slightly broad based with outward extending apices. Margins: Finely serrated. Color: Yellow-Green Group 144A.

*Petiole*.—Length: 22 mm. Diameter: 2 mm.

*Upper surface*.—Color: Greyed-Purple Group 184B.

*Lower surface*.—Color: Yellow-Green Group 146C.

*Rachis*.—Length: 45 mm. Upper surface: Color: Greyed-Purple Group 184B.

*Lower surface*.—Color: Yellow-Green Group 146C.

*Leaflet*.—Quantity: Normal number of leaflets leaves in middle of the stem is 5 leaflets. Margins: Serrated. Size: Average size of the terminal leaflet on normal leaves is 50 mm in length by 36 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Miniature rose class named 'Poulpar084', substantially as illustrated and described herein, due to its abundant yellow flowers, disease resistance, and extended period of bloom.

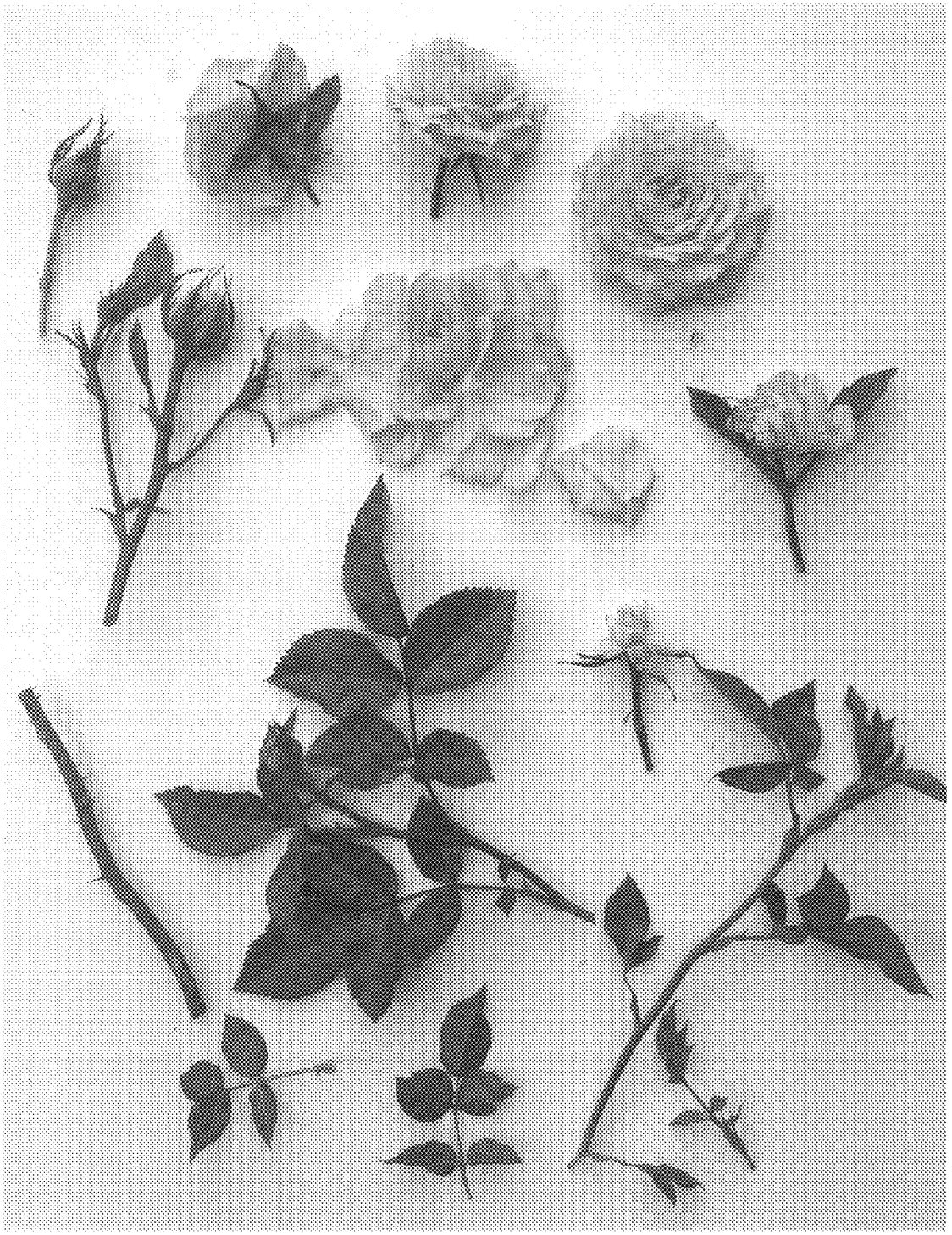

* * * * *